(12) United States Patent  
Filipovic et al.

(10) Patent No.: US 9,086,847 B2  
(45) Date of Patent: Jul. 21, 2015

(54) PERSONAL CLOUD CASE COVER WITH A PLURALITY OF MODULAR CAPABILITIES

(71) Applicant: Micro Mobio Corporation, Palo Alto, CA (US)

(72) Inventors: Zlatko Aurelio Filipovic, Palo Alto, CA (US); Weiping Wang, Palo Alto, CA (US); Adam James Wang, Palo Alto, CA (US)

(73) Assignee: Micro Mobio Corporation, Palo Alto, CA (US)

( * ) Notice: Subject to any disclaimer, the term of this patent is extended or adjusted under 35 U.S.C. 154(b) by 99 days.

(21) Appl. No.: 13/831,663

(22) Filed: Mar. 15, 2013

(65) Prior Publication Data

US 2014/0087788 A1    Mar. 27, 2014

Related U.S. Application Data

(60) Provisional application No. 61/705,383, filed on Sep. 25, 2012.

(51) Int. Cl.
```
H04M 1/02      (2006.01)
G06F 1/16      (2006.01)
H04B 1/3888    (2015.01)
H04M 1/18      (2006.01)
```

(52) U.S. Cl.
CPC ............ *G06F 1/1633* (2013.01); *G06F 1/1628* (2013.01); *G06F 1/1632* (2013.01); *G06F 1/1698* (2013.01); *H04B 1/3888* (2013.01); *H04M 1/0254* (2013.01); *H04M 1/185* (2013.01)

(58) Field of Classification Search
CPC . G06K 19/0723; H04W 84/18; H04W 16/14; H04W 88/06; H04W 88/02; H04M 1/72519; H04M 1/0254; H04B 1/3888
USPC .............. 455/550.1, 552.1, 41.1–41.2, 553.1, 455/556.1–556.2, 557, 558, 502, 410, 411, 455/414.1, 3, 6
See application file for complete search history.

(56) References Cited

U.S. PATENT DOCUMENTS

| | | |
|---|---|---|
| 6,442,018 B1 | 8/2002 | Dinkin |
| 7,743,999 B1 | 6/2010 | Griffin |
| 2003/0115475 A1* | 6/2003 | Russo et al. .................. 713/186 |
| 2004/0184466 A1* | 9/2004 | Chang et al. .................. 370/401 |
| 2012/0088557 A1 | 4/2012 | Liang |
| 2012/0212896 A1 | 8/2012 | Schulz |
| 2012/0218695 A1* | 8/2012 | Sakai ....................... 361/679.01 |
| 2012/0235635 A1 | 9/2012 | Sato |
| 2012/0241247 A1 | 9/2012 | Choe |
| 2012/0247989 A1 | 10/2012 | Cooper |
| 2012/0249064 A1* | 10/2012 | Negishi et al. ................ 320/108 |
| 2012/0252411 A1* | 10/2012 | Johnsgard et al. ............ 455/411 |
| 2012/0262345 A1 | 10/2012 | Byun et al. |
| 2012/0268891 A1 | 10/2012 | Cencioni |
| 2012/0270600 A1 | 10/2012 | Zelson |
| 2012/0281356 A1 | 11/2012 | Brewer et al. |
| 2012/0299966 A1* | 11/2012 | Kim et al. .................... 345/660 |
| 2013/0063873 A1 | 3/2013 | Wodrich et al. |

(Continued)

*Primary Examiner* — Cong Tran  
(74) *Attorney, Agent, or Firm* — Roark IP

(57) ABSTRACT

A personal cloud contained in a case for a portable computing device such as a tablet personal computer (PC), mobile phones, portable media players, or the like. The personal cloud case may be fitted with memory, a network connection, two-way wireless charging, external memory slots, external connections and other components for portable personal cloud computing.

21 Claims, 8 Drawing Sheets

(56) References Cited

U.S. PATENT DOCUMENTS

| | | |
|---|---|---|
| 2013/0076614 A1 | 3/2013 | Ive et al. |
| 2013/0288600 A1* | 10/2013 | Kuusilinna et al. .......... 455/41.2 |
| 2014/0086586 A1* | 3/2014 | Voutilainen et al. .......... 398/115 |
| 2014/0159867 A1 | 6/2014 | Sartee et al. |

* cited by examiner

US 9,086,847 B2

PERSONAL CLOUD CASE COVER WITH A PLURALITY OF MODULAR CAPABILITIES

PRIORITY CLAIM

This patent application claims the benefit of the U.S. provisional patent application having Ser. No. 61/705,383, filed Sep. 25, 2012; the aforementioned application being incorporated by reference in its entirety.

FIELD OF THE DISCLOSURE

The present disclosure relates generally to mobile computer covers and, in particular, in one or more embodiments, the present disclosure relates to cases having a plurality of electronic component accessories.

BACKGROUND

There are presently a wide variety of portable electronic devices 102 as disclosed in FIG. 1A. The portable electronic devices may include cellphones such as the iPhone®, Nexus, Lumia and the like and tablet personal computers (PCs) such as the iPad®, Kindle® and similar type devices. These portable electronic devices are often protected by a simple case cover 104 as disclosed in FIG. 1B. These prior art case covers 104 typically do not contain any functional components beyond the protective cover itself.

SUMMARY

An embodiment disclosed herein is directed toward a case for a mobile computing device comprising: a first panel and a second panel capable of forming a compartment for the mobile computing device; and the first panel including a charging unit capable of wirelessly charging the mobile computing device.

Another embodiment is directed toward a panel for connecting to a mobile computing device comprising: a plurality of attachments capable of coupling the panel to the mobile computing device; a plurality of electronic components which are capable of wireless linking to the mobile computing device and to other electronic devices; and a power source coupled to the plurality of electronic components and capable of providing power these electronic components. In this embodiment the plurality of components may include memory, a WLAN modem which is capable of wirelessly sending and receiving to and from the mobile computing device, and a WWAN modem which is capable of wirelessly sending and receiving signals to and from the mobile computing device.

Another embodiment is directed toward a case for a mobile computing device comprising: a plurality of panels capable of forming a compartment for the mobile computing device; a charging unit mounted on one of the plurality of panels and capable of wirelessly charging the mobile computing device and receiving charge from the mobile computing device; a power source mounted on one of the plurality of panels and connected to the charging unit and capable of storing power received from the charging unit and providing power to the charging unit; the power source connected to a plurality of modules located on at least one of the plurality of panels and capable of providing power to the modules; and wherein the plurality of modules include a WLAN modem which allows the case to wirelessly transmit and receive signals from other electronic devices.

DETAILED DESCRIPTION

Although particular aspects or features of the following disclosure may be described with reference to one or more particular embodiments and/or drawings, it should be understood that such features are not limited to usage in the one or more particular embodiments or drawings with reference to which they are described, unless expressly specified otherwise. The functionality and/or the features of the embodiments that are described may be alternatively embodied by one or more other devices which are described but are not explicitly described as having such functionality/features.

Current mobile computing device covers are limited in their functionality by mainly providing protection from environmental shocks for mobile computing devices. However, the personal cloud cover case (or "PCCC") as disclosed in this application by providing electronic component accessories and functionalities to the cover case enhances the ability of a mobile computing device located inside the PCCC to provide cloud computing services. Cloud computing is the use of computing resources that are delivered as a service over a network (such as the Internet) and which reside in the "cloud". The mobile computing device in the case could be an iPad®, iPhone®, PC tablet, Android® based tablet, TouchPad, Nexus 7®, Slate® or the like.

Figure 1B:
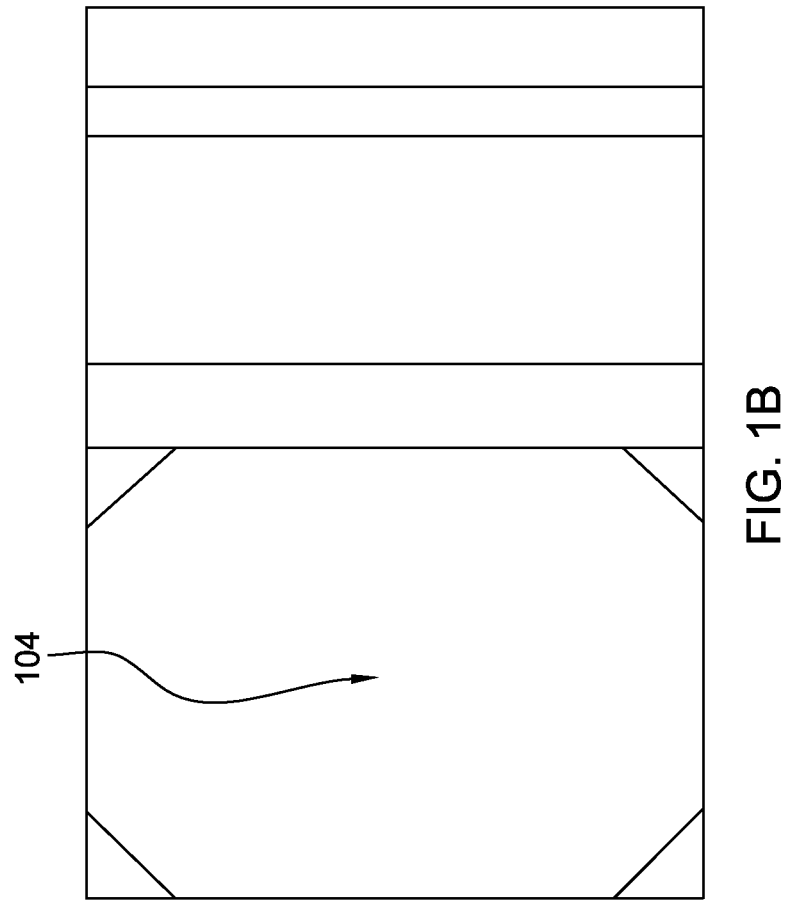
FIG. 1B is a front view of a prior art simple case cover for a mobile computing device.
Figure 1A:
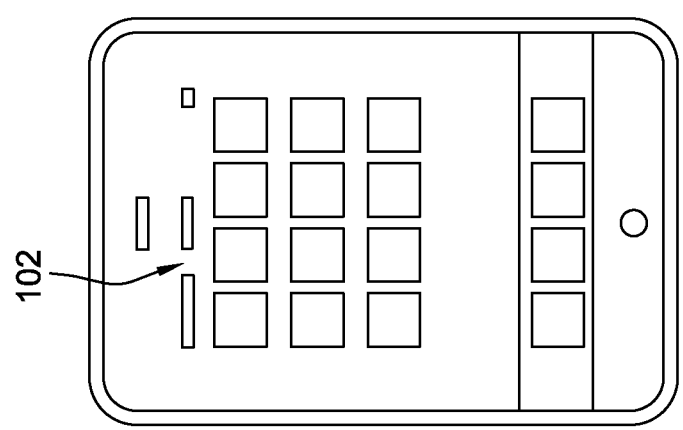
FIG. 1A is a front view of a prior art mobile computing device.
Figure 2A:
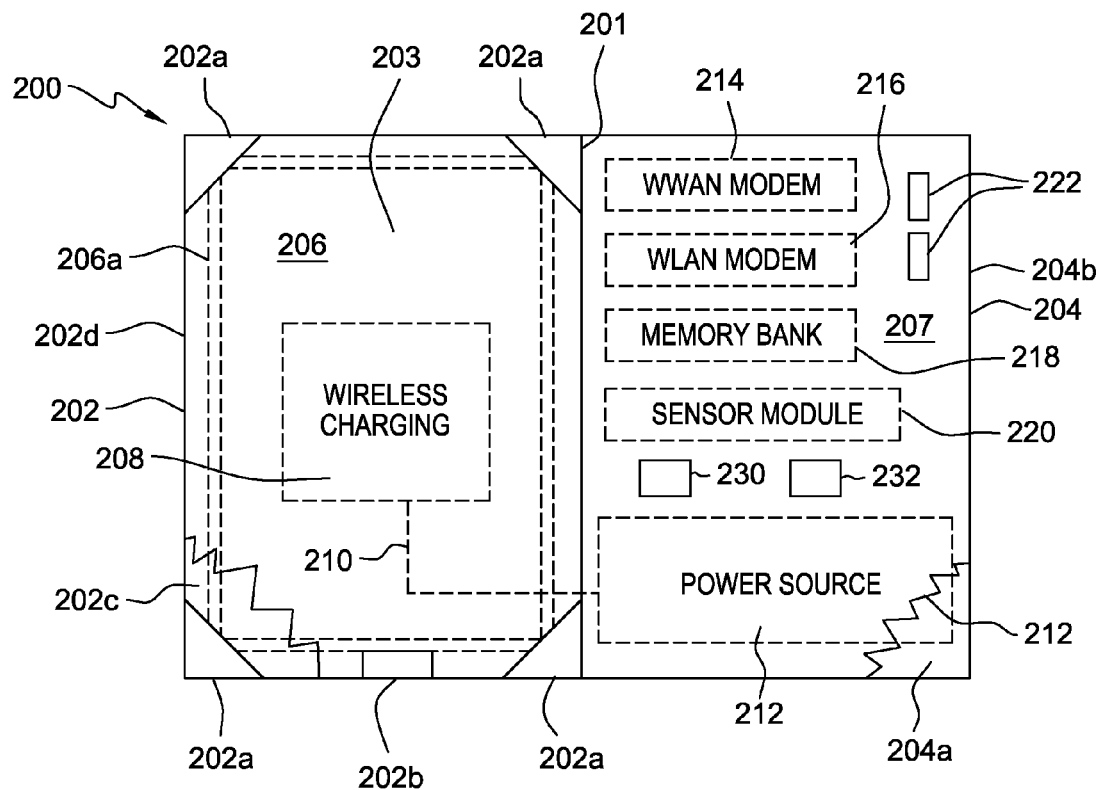
FIG. 2A is a front view of a personal cloud case cover (PCCC).

FIG. 2A is a front view of a PCCC 200 which is shown in an open position. The case 200 provides a personal cloud to the user and access to a wireless network (such as 3G, 4G, WiFi, SuperWifi, and similar technologies) of a mobile computing device (not shown) stored in the case 200. The case 200 may be made of any material (hard and/or soft) that makes the case lightweight but durable and resilient such as plastic, silicone, ceramic, fabric, leather, steel, aluminum, fiberglass, titanium, Kevlar, or rubber. The case 200 could be a continuous piece of material with a flexible (or bendable) area 201 located between two opposing panels (first panel 202 and second panel 204) which pivot together around a compartment 203 for containing the mobile computing device. In an alternative embodiment, the case 200 could be made up of plurality of attached sections (201, 202 and 204). First panel 202 also has 4 sleeves 202a to hold the mobile computing device in place in the case 200. In alternative embodiments, the mobile computing device could be attached to the PCCC 200 using a plurality of magnets (instead of the sleeves 202a) positioned under the mobile device, rubber straps or other similar attachment methods.

The first panel 202 is constructed in layers and includes inner first panel layer 202c, outer first panel layer 202d and embedded circuit board 206. Typically, from the front view the circuit board 206 cannot be seen since it is located underneath the first panel layer 202c shown in cutaway but which is designed to cover substantially the entire first panel 202. An antenna 206a is located on the circuit board 206 and may be in contact with the mobile communication device wirelessly, through physical contact or by connector 202b. Connector 202b is optional and in alternative embodiments it would not be present. The antenna 206a will allow for better transmission and reception on the part of the mobile communication device. The antenna 206a can be a "chip" antenna, printed circuit board (PCB) antenna or the like covering a plurality of wireless bands (e.g., 400 MHz-3.6 GHz). Alternatively, a PCB antenna may be used, and the antenna 206a will be printed directly onto the circuit board 206. Also located on the board 206 is a two-way wireless charging unit 208 which is in substantial proximity to the resting place of the mobile communication device in the cover 200. The charging unit 208 is designed such that when the mobile communication device is in proximity to the charging unit an electromagnetic field generated by the charging unit pulls the communication device into proper position and alignment for optimal charging (i.e., charging coil alignment). The wireless charging unit 208 is connected through a bidirectional electrical link 210 to power source 212 located on a circuit board 207 embedded in the second panel 204. The bidirectional electrical link 210 is an example of the plurality of electrical connections that are made throughout the case 200 but which are not necessarily shown in the Figures. Link 210 might be in the form of a ribbon cable so as not to be damaged with the opening and closing of the case 200. The wireless charging unit 208 is capable of wirelessly charging the mobile communication device with power received from the power source 212 or wirelessly receive power from the mobile communication device and transfer it to the power source 212. The wireless charging unit 208 may operate by magnetic resonance, inductive charging, or power over radio frequency (RF) or similar wireless charging methods. The power source 212 is used to power the plurality of components located throughout the cover 200 and, as described, can also be used as a backup battery for the mobile computing device when the voltage in the battery of the mobile computing device falls below a predetermined level.

The second panel 204 can be made up of an inner second panel 204a and an outer second panel 204b containing the embedded circuit board 207 but which typically cannot be seen from a front view since it is covered by inner second panel layer 204a. The inner second panel layer 204a covers substantially the entire second panel 204 but is only partially shown in cutaway so as to illustrate the components mounted on the circuit board 207 in the outer second panel 204b. It should be understood that the inner second panel layer 204a and the outer second panel layer 204b can be coupled together by a variety of methods such as ultrasonic bonding, mechanical fasteners, adhesives, or solvents. In alternative embodiments, the inner second panel 204a may be entirely or substantially detachable from the outer second panel 204b; the inner second panel 204a may be a closure flap that is fastened close by means of adhesive, a snap button, or Velcro or the inner second panel 204a may not be present at all so as to allow easy access to the components mounted on the board 207 in the outer second panel 204b. The case 200 may further be made up of a plurality of modules 214, 216, 218 and 220 mounted on the circuit board 207 which allow the PCCC 200 to have multi-functional capability. The modules may be made of low profile components which help minimize the thickness of the cover. The plurality of modules may be permanently mounted, may snap-in to the board 207 or may be some combination thereof. First module 214 may include a wireless wide area network modem (WWAN). The WWAN could include baseband, a radio frequency integrated circuit (RFIC), a radio frequency front-end module (RF FEM), Envelope Tracking (ET), Power Management IC (PMIC), and other connected components to link the mobile computing device to a mobile network such as a 3G, 4G or future generation network. Second module 216 may include a wireless local area network (WLAN) modem for a mobile computing device to connect to a local router and then to 2G, 3G and 4G networks. The WLAN modem can be baseband, RFIC, RF FEM and other connectivity components. The case 200 may contain near field communications (NFC) technology which may be used for contactless shortrange communications based on RF identification standards (RFID) using magnetic field induction to enable communication between the electronic components in the case 200 over short distances such as a few centimeters. In other embodiments, the WLAN modem connection could be made using wireless protocols such as WiFi, SuperWiFi (i.e., the next generation WiFi with superior range), Bluetooth, wireless for high definition multimedia interface (WHDMI), or the like. Third module 218 may be internal storage such as solid-state drives (SSD) or flash memory (e.g., MultiMedia Card (MMC), electronic MMC (eMMC) or the like). Fourth module 220 may contain a sensor chip that is able to detect biometrics inputs such as finger prints, eye movement, face shape, and the like. Module 220 can be used for functions such as a security feature for allowing or denying access to the electronic components in the case, gaming, and medical purposes (e.g., measuring blood cell count and the like). The second panel 204 may also include a smart feature such as a synchronization input 230 (e.g., such as a button, touch screen, or the like) that allows the plurality of electronic components (e.g., module 218) in the PCCC 200 to be synched to other networked devices in the cloud when operated. This input 230 would primarily be used when a mobile communication device is not present in the PCCC 200. The input 230 may be used to backup data stored in the components of the PCCC 200. Reference 232 in FIG. 2A shows a controller which may be used with the mobile communication device or in the absence of the mobile device to control the electronic components in the PCCC 200. For example, in the synching process when input 230 is operated the controller 232 would direct the synching operation.

Figure 2B:
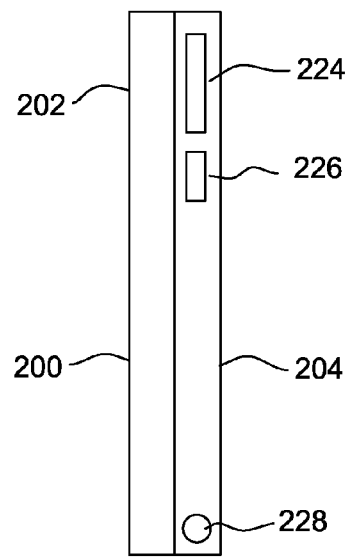
FIG. 2B is a side view of the PCCC of FIG. 2A.

FIG. 2B is a side view of the case 200 in a closed position. Data connection ports 224 and 226 provide communication capabilities to the case 200. Ports 224 and 226 may be a mini universal serial bus (USB), micro universal USB port or an audio visual (AN) connector such as a high definition multimedia interface (HDMI) port and the like. Charging port 228 can be connected to the grid or other power source to feed the power source 212.

Figure 3:
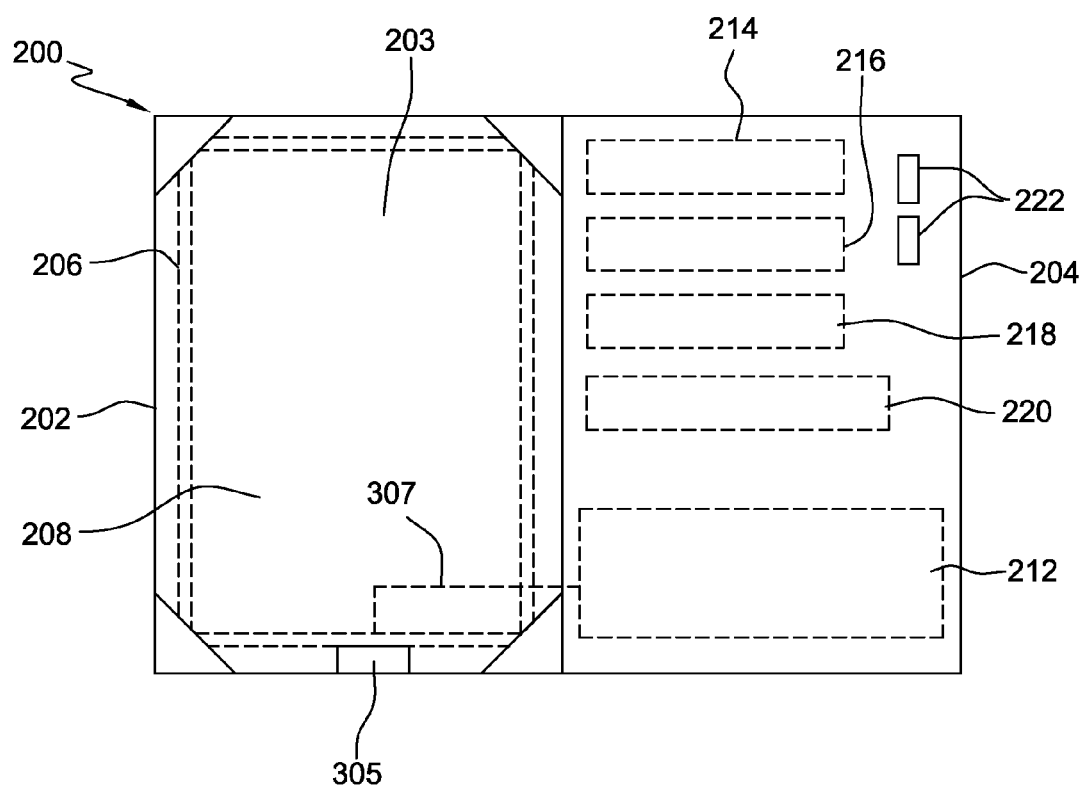
FIG. 3 is a front view of a second embodiment of the PCCC.

FIG. 3 is a second embodiment of the PCCC 200. Common numbering is used in FIGS. 3 through 9 and FIGS. 2A to 2B to denote similar elements. In this second embodiment, instead of wireless charging, a docking bay 305 having a set of electrical contacts is configured to electrically engage with the input/output contacts on a mobile communication device. The docking bay 305 may be a standard connector that allows the mobile communication device to receive power through line 307 from power source 217.

Figure 4:
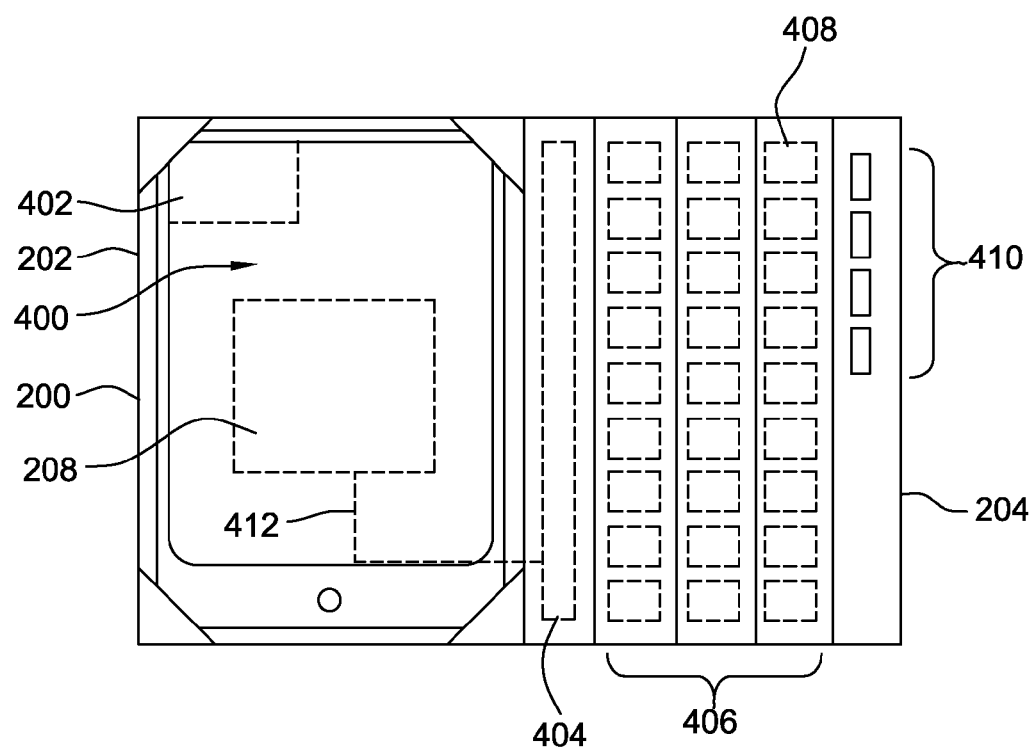
FIG. 4 is a front view of a third embodiment of the PCCC.

FIG. 4 illustrates a third embodiment of the PCCC 200. A mobile communication device 400 can be connected to a local area or wide area network through wireless modem 402 which may be 3G, 4G, 3G/4G, WHDMI, Bluetooth, WiFi, SuperWiFi, and other wireless standard. Module 404 is a replaceable, rechargeable battery that is charged through line 412 from the wireless charger 208 and receives power from mobile communication device 400. Module 404 performs the same function as power source 212 in FIG. 2 but is arranged differently in the case 200 as shown in FIG. 4. The wireless charger 208 may be located on the first panel 202 beneath the mobile communications device 400. The module 404 can also be charged from a power outlet when the case 200 is plugged in. The module 404 can be used as a power source for other modules (reference numerals 408 and 410 as discussed below) located in the case 200. An embedded memory bank 406 includes a plurality of memory modules and is mounted on the second panel 204. The memory bank modules may be 500 MegaByte (MB), 1 Gigabyte (GB), 1 Terrabyte (TB) or the like in memory size. Memory slots 410 are capable of holding additional memory such as removable micro-Secure Digital (micro-SD) memory cards for storage expansion.

Figure 5:
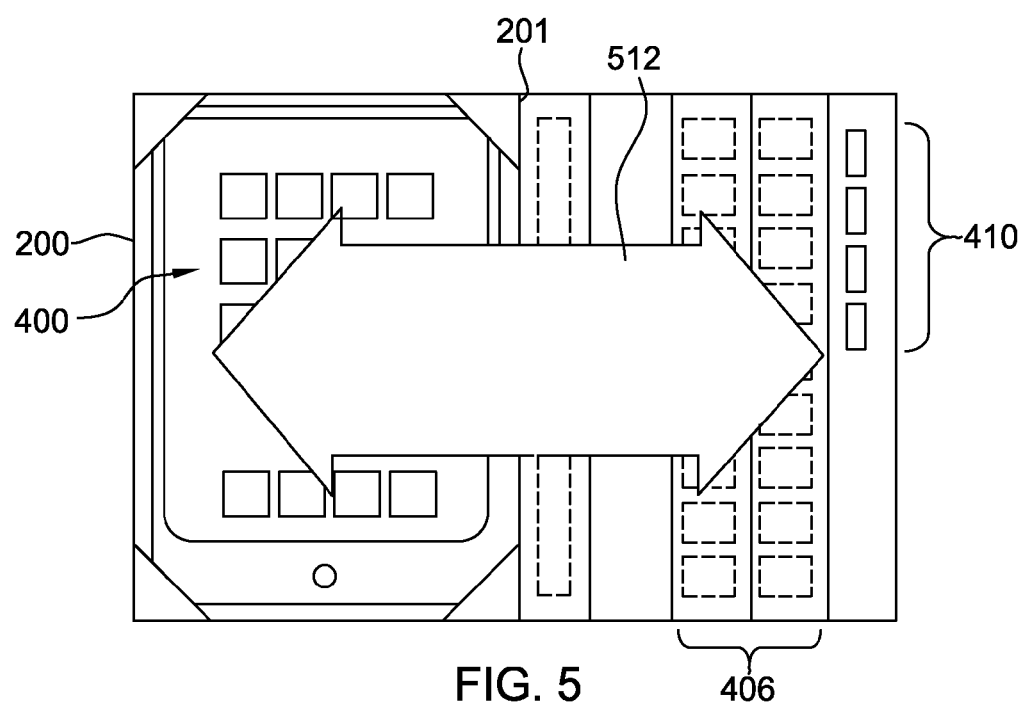
FIG. 5 is a front view of a fourth embodiment of the PCCC.

FIG. 5 illustrates a fourth embodiment of the PCCC 200 which demonstrates that the plurality of modules are detachable and could be two instead of three in the case 200. Also, FIG. 5 discloses a wireless data connection 512 between the device 400 and memory bank 406 using WiFi, SuperWiFi or Bluetooth protocols. In alternate embodiments, the data connection 512 could be a hardwired such as a Universal Serial Bus (USB), microUSB, miniUSB, or HDMI (with the data line being flexibly bendable across the flexible region 201 in the form of a ribbon cable or the like). In other embodiments, the connection could also be an optical wireless link or cable such as infrared. The data transfer could be bi-directional to allow for read and write both ways from device 400 to memory 406 and from memory 406 to device 400.

Figure 6A:
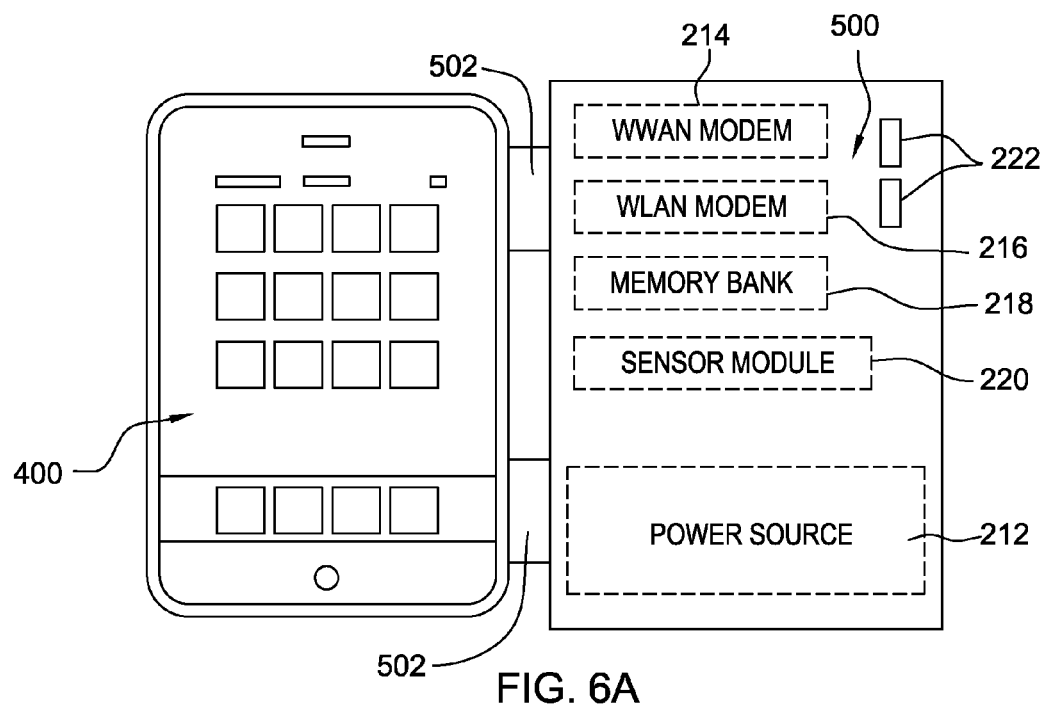
FIG. 6A is a front view of a fifth embodiment of the PCCC.
Figure 6B:
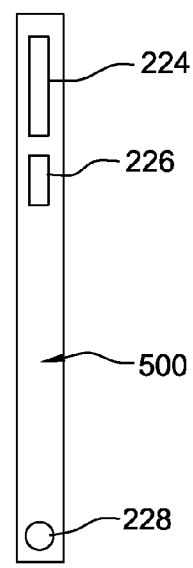
FIG. 6B is a side view of the PCCC of FIG. 6A.

FIG. 6A is another embodiment of the PCCC with just one panel 500 attached to the device 400 through attachments 502. Attachments 502 may be magnets, clip ins, connectors or some other type of hinge. The attachments 502 may internally include a plurality of electrical links to provide power from the power source 212 to the mobile communication device 400 as well as provide data communications between the modules on the panel 500 and the device 400. The power source 212 may include a wireless charging unit so as to wirelessly charge the device 400. The charging may take place when the panel 500 is in a lateral position relative to the device 400 as shown in FIG. 6A. In an alternative embodiment, the panel 500 may be folded over and placed in contact with the device 500 to establish an electrical power link between the power source 212 and electrical contacts located on the device 400. Also, similar to the embodiment of FIG. 5, a wireless data connection may be established between the device 400 and the plurality of modules on the panel 500 (items 214, 216, 218, 220, and 222). FIG. 6B is a side view of the panel 500 showing the connection ports 224, 226, and 228 which serve the same functions as described in connection with FIG. 2B above.

Figure 7:
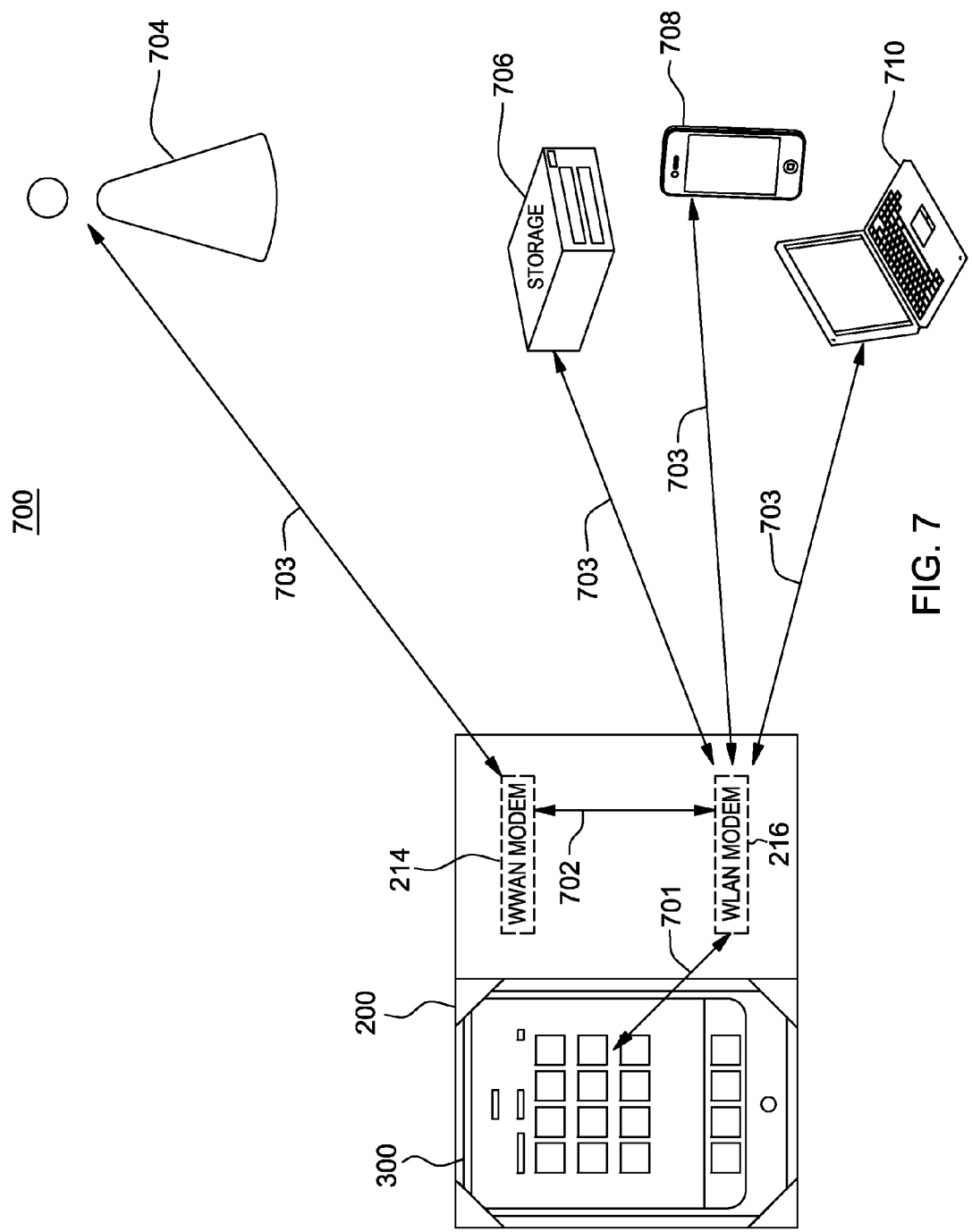
FIG. 7 is a schematic diagram of a PCCC in a cloud/networked environment utilizing 3G, 4G and similar wireless connections.

FIG. 7 illustrates the mobile communication device 300 and PCCC 200 operating in a cloud (or networked) environment 700. Storage 706, mobile phone 708 and personal computer (PC) 710 are part of the cloud upon which the mobile communications device 300 and PCCC 200 can exchange data and synchronize through a plurality of wireless links 703. The WWAN modem module 214 and the WLAN modem module 216 of FIG. 7 operate in a similar manner as described in connection with FIG. 2A above. The mobile computing device 300 communicates through a bi-directional wireless link 701 with the WLAN modem 216 using Bluetooth, WiFi, SuperWiFi and similar wireless standards. In another embodiment, the link 701 may be a wired link. WLAN modem 216 then can read and write wirelessly in a local environment with storage 706. The WLAN modem 216 can also communicate with another mobile phone 708 and PC 710. Alternatively, the mobile computing device 300 can communicate through WLAN 216 over a bi-directional link 702 with WWAN modem 214. WWAN modem 214 can communicate wirelessly using 3G/4G protocols over longer distances than the WLAN modem 216 with a cell tower 704 and then to the Internet. In the environment of FIG. 7, the case 200 is acting as "hotspot". As a hotspot, the case 200 offers network (e.g., Internet) access over the WWAN modem 214 or WLAN modem 216.

Figure 8:
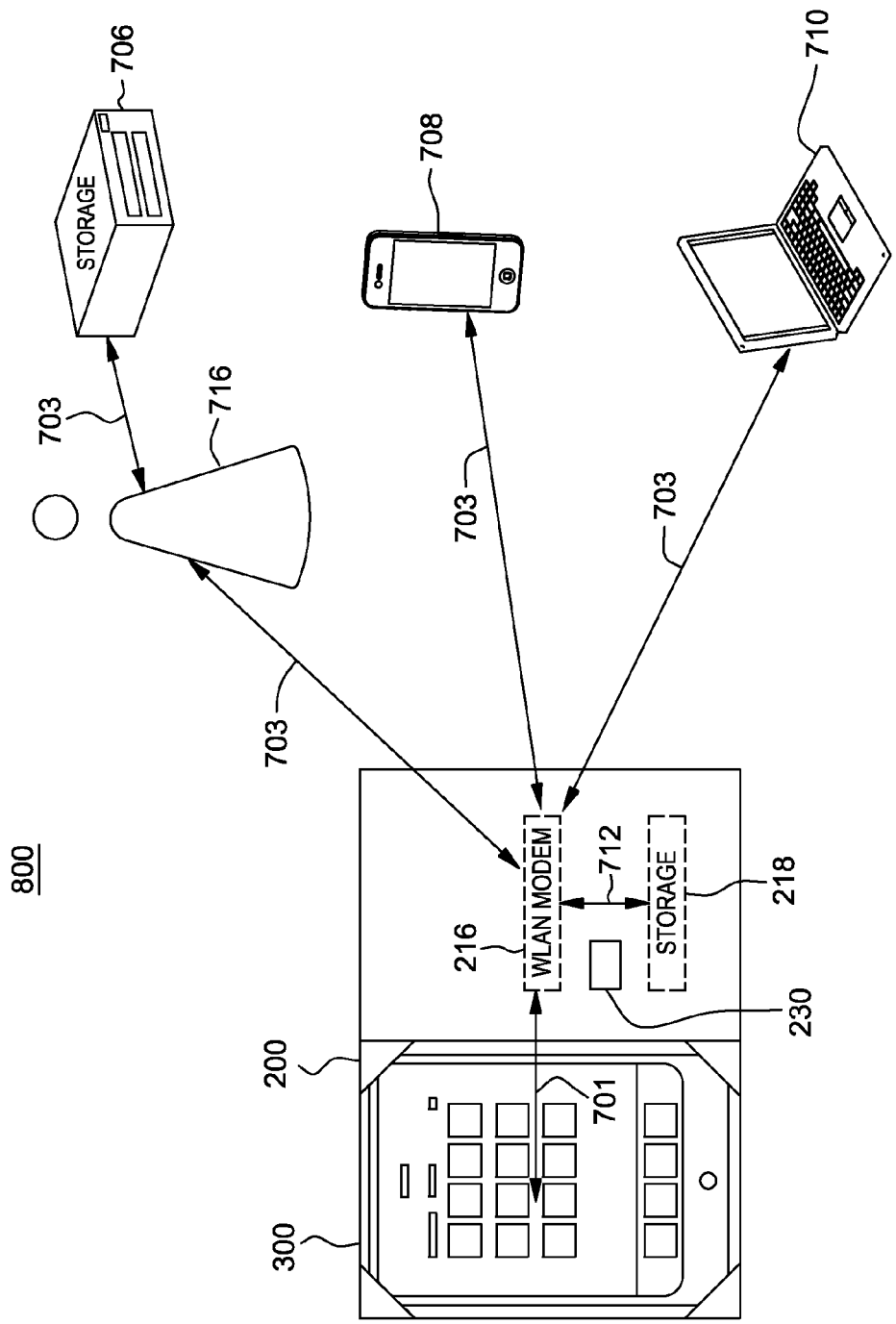
FIG. 8 is a schematic diagram of the PCCC in another cloud/networked environment system.

FIG. 8 illustrates another variation of the mobile communication device 300 and the case 200 in operation 800. This arrangement allows the local storage 218 to have access to a plurality of devices in the cloud such as the communication device 708, PC 710 and storage 706 through local wireless router (or access point) 716. As previously discussed in connection with FIG. 2A, sync input 230 can be operated when the mobile communication device is not present in the case 200 to backup all data contained in the components in the case 200 to the cloud (e.g., devices such as 706, 708, 710 and other devices). Another advantage is that this system allows for the formation of a "pass through Internet" from the mobile communication device 300 to devices 706, 708, 710 and a network (e.g., the Internet). WLAN modem 216 is connected to memory storage 218 through link 712 and is capable of establishing wireless communications with both the mobile communication device 300 and the devices 706, 708, and 710. In operation, the mobile communication device 300 establishes a wireless connection 701 through WiFi, SuperWiFi, 4G or the like to the WLAN modem 216. Through WLAN modem 216, the communication device 300 is capable of connecting to the memory storage 218 (e.g., providing information or instructions regarding reading and/or writing) while simultaneously browsing the Internet through wireless link 703 to access point 716. The term simultaneously as used herein shall mean immediate or nearly immediate succession in time. In another embodiment, the connection from the mobile communication device to the memory storage 218 could be wired. Alternatively, the communication device could be simultaneously connecting to memory storage 218 while communicating with devices 706, 708 and 710 through wireless links 703. This pass through Internet feature allows the user to access data stored in the memory 218 and browse the Internet simultaneously from a single device (mobile communication device 300) or a plurality of devices. The WLAN modem 216 is designed to operate in one or more bands and cover one or more wireless standards. The bands may include first and second frequency bands (e.g., 2 GHz and 5 GHz). The WLAN modem 216 may use the first band for the transmission of information from memory storage 218 to the mobile communication device 300 and the second band for communications with the access point 716 (and thereby the Internet).

Figure 9:
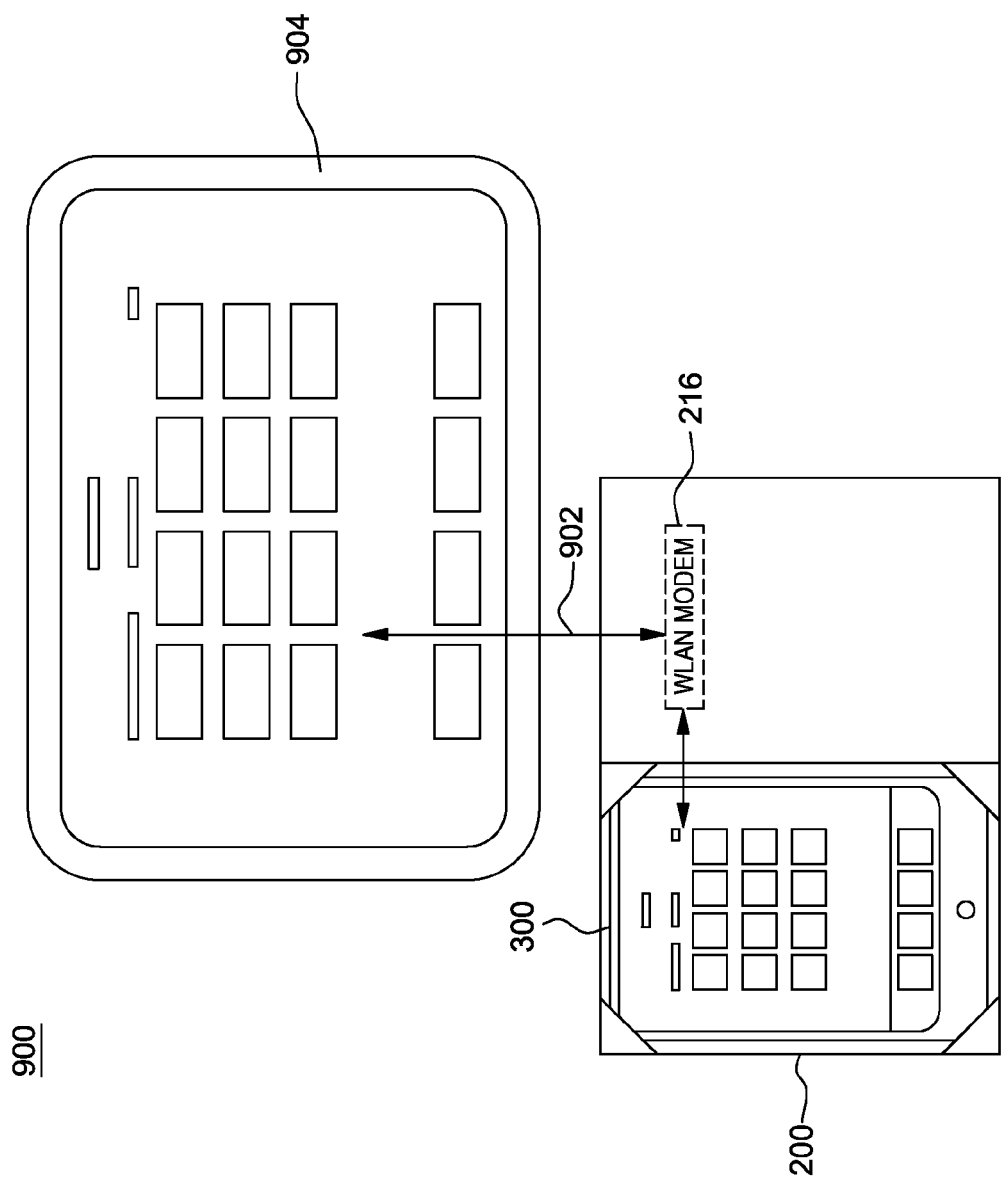
FIG. 9 is view of the PCCC operating with a large external monitor.

FIG. 9 illustrates another environment 900 in which the PCCC 200 may operate. The PCCC 200 allows the mobile communication device 300 to link through WLAN 216 and wireless link 902 with large external monitor 904 using WiFi, SuperWiFi, WHDMI, or the like and display information (e.g., video, audio, or text) from either the mobile communication device 300, the memory storage or another source (e.g., devices 706, 708, 710) on to the monitor 904.

In this disclosure, devices that are described as in "communication" with each other or "coupled" to each other need not be in continuous communication with each other or in direct physical contact, unless expressly specified otherwise. On the contrary, such devices need only transmit to each other as necessary or desirable, and may actually refrain from exchanging data most of the time. For example, a machine in communication with or coupled with another machine via the Internet may not transmit data to the other machine for long period of time (e.g. weeks at a time). In addition, devices that are in communication with or coupled with each other may communicate directly or indirectly through one or more intermediaries.

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Moreover, the illustration of a process by its depiction in a drawing does not imply that the illustrated process is exclusive of other variations and modifications thereto, does not imply that the illustrated process or any of its steps are necessary to the embodiment(s), and does not imply that the illustrated process is preferred.

The foregoing description and embodiments have been presented for purposes of illustration and description and are not intended to be exhaustive or to limit the embodiments in any sense to the precise form disclosed. Also, many modifications and variations are possible in light of the above teaching. The embodiments were chosen and described to best explain the principles of the disclosure and its practical application to thereby enable others skilled in the art to best use the various embodiments disclosed herein and with various modifications suited to the particular use contemplated. The actual scope of the invention is to be defined by the following claims.

The invention claimed is:

1. A case for a removable mobile computing device comprising:
    a first panel and a second panel capable of forming a compartment for the removable mobile computing device;
    the first panel including a charging unit capable of wirelessly charging the removable mobile computing device;
    a detachable WLAN modem module mounted on the second panel which is capable of wirelessly sending and receiving signals to and from a local network; and
    a detachable WWAN modem module mounted on the second panel which is capable of wirelessly sending to and receiving signals from a cellular network and which is mounted on the second panel.

2. The case of claim 1, wherein the charging unit is also capable of receiving power from the removable mobile computing device and transferring the power to a power source located in the case.

3. The case of claim 1, further comprising:
    a power source capable of receiving a charge from the charging unit; and wherein the power source is configured to provide power to a plurality of electronic components mounted in the case.

4. The case of claim 1, further comprising:
    an antenna embedded in the first panel and capable of coupling the mobile computing device to the cellular network.

5. The case of claim 4, wherein the wireless network may be selected from the group consisting of: 2G, 3G and 4G.

6. The case of claim 1, wherein the cellular network may be selected from the group consisting of: 2G, 3G and 4G.

7. The case of claim 1, further comprising:
    a memory bank capable of being wirelessly coupled to the removable_mobile communication device; and
    wherein the memory bank includes a plurality of memory modules.

8. The case of claim 7, wherein the plurality of memory modules are replaceable.

9. The case of claim 7, wherein the plurality of memory modules are capable of backing up information stored on the removable mobile communication device.

10. The case of claim 1, wherein the charging unit is also capable of receiving power from the removable mobile computing device and transferring the power to a power source located in the case; and wherein the power source is configured to provide power to a plurality of electronic components mounted in the case.

11. The case of claim 1, further comprising:
    a circuit embedded in the case which is capable of forming a data link between the removable mobile computing device and the detachable WWAN modem.

12. The case of claim 1, further comprising:
    a sensor chip configured to detect biometric inputs selected from the group consisting of: fingerprints, eye movement, and face shape; and
    wherein the sensor chip provides a security function to deny unauthorized access to a plurality of components in the case.

13. The case of claim 1, wherein the WLAN modem may be from the group consisting of: WiFi or SuperWiFi.

14. The case of claim 1, further comprising:
    a plurality of electronic components; and
    an input configured to synchronize the plurality of electronic components with at least one storage device.

15. The case of claim 1, wherein the case is substantially made of a fabric material.

16. The case of claim 1, wherein the wireless charging unit is configured to pull the removable mobile device into proper alignment for charging.

17. The case of claim 1, wherein the detachable WWAN modem module and detachable WLAN modem module are capable of being snapped into position on the second panel.

18. A case for a removable mobile computing device comprising:
    a plurality of panels capable of forming a compartment for the removable mobile computing device;
    a charging unit mounted on one of the plurality of panels and capable of wirelessly charging the removable mobile computing device and receiving charge from the removable mobile computing device;
    a power source mounted on one of the plurality of panels and connected to the charging unit and capable of storing power received from the charging unit and providing power to the charging unit;
    a detachable WLAN modem module mounted on one of the panels which is coupled to the power source and which is configured to wirelessly send to and receive signals from a local network when the removable computing device is not present in the case; and
    a detachable WWAN modem module mounted on one of the panels which is coupled to the power source and which is configured to wirelessly send and receive signals to and from a wireless network when the mobile computing device is not present in the case.

19. A case for a removable mobile computing device and a hotspot comprising:
the removable mobile computing device; and
a plurality of panels capable of forming a compartment for the mobile computing device; and
wherein at least one of the plurality of panels has a WWAN modem which is configured to wirelessly transmit signals to and receive signals from a network both when the removable mobile computing device is present and is not present.

20. A case for a removable mobile computing device comprising:
first and second panels capable of forming a compartment for the removable mobile computing device;
the second panel having an inner second panel layer and outer second layer panel layer with a second panel circuit board located in between and wherein the second panel circuit board has a detachable WLAN modem module and memory storage mounted thereon; and
wherein the memory storage is capable of connecting through the WLAN modem module to a network.

21. The case of claim 20, wherein
the WLAN modem is configured to operate in a plurality of bands and wireless standards, the plurality of bands including a first band and a second band;
the first band is used when the WLAN modem is transmitting information from the memory storage to the mobile computing device;
the second band is used when the WLAN modem is transmitting and receiving the wireless communications from the network; and
wherein the second band is greater than the first band.

* * * * *